(12) United States Patent
Vadai et al.

(10) Patent No.: US 9,370,460 B2
(45) Date of Patent: Jun. 21, 2016

(54) SYSTEMS AND METHODS FOR TREATING AMBLYOPIA BY VISUAL STIMULATION OF THE BRAIN

(71) Applicant: Visior Technologies, LTD, Herzliya (IL)

(72) Inventors: Ilan Vadai, Hod-Hasharon (IL); Yuval Avni, Tel-Aviv (IL)

(73) Assignee: Visior Technologies, LTD (IL)

( * ) Notice: Subject to any disclaimer, the term of this patent is extended or adjusted under 35 U.S.C. 154(b) by 0 days.

(21) Appl. No.: 14/427,888

(22) PCT Filed: Sep. 15, 2013

(86) PCT No.: PCT/IL2013/050777
§ 371 (c)(1),
(2) Date: Jul. 16, 2015

(87) PCT Pub. No.: WO2014/041545
PCT Pub. Date: Mar. 20, 2014

(65) Prior Publication Data
US 2015/0305964 A1  Oct. 29, 2015

Related U.S. Application Data

(60) Provisional application No. 61/827,594, filed on May 26, 2013, provisional application No. 61/700,903, filed on Sep. 14, 2012.

(51) Int. Cl.
*G09G 5/00* (2006.01)
*A61H 5/00* (2006.01)
(Continued)

(52) U.S. Cl.
CPC *A61H 5/00* (2013.01); *A61B 3/032* (2013.01); *A61B 3/08* (2013.01); *A61B 3/085* (2013.01);
(Continued)

(58) Field of Classification Search
None
See application file for complete search history.

(56) References Cited

U.S. PATENT DOCUMENTS

| 4,726,672 A * | 2/1988 | O'Brien | A61H 5/00 351/203 |
| 2004/0076942 A1* | 4/2004 | O'Neil | G09B 7/00 434/350 |

(Continued)

FOREIGN PATENT DOCUMENTS

| WO | 03098529 A2 | 11/2003 |
| WO | 2007043047 A2 | 4/2007 |

(Continued)

OTHER PUBLICATIONS

International Search Report for Application No. PCT/IL2013/050777 dated Dec. 31, 2013.

(Continued)

*Primary Examiner* — William Beutel
(74) *Attorney, Agent, or Firm* — Lerner, David, Littenberg, Krumholz & Mentlik, LLP

(57) ABSTRACT

A system for treating amblyopia through the visual stimulation of the brain through a predetermined regime is provided. The system for treating amblyopia comprises a headmountable visual content display device, a controller unit, a visual content source, a data storage device, a graphic processing unit and an audio source. A protocol useful for treating amblyopia by visual stimulation of the brain is also provided. A predetermined regime useful for treating amblyopia by stimulation of the brain is additionally provided.

23 Claims, 12 Drawing Sheets

(51) Int. Cl.
*A61B 3/08* (2006.01)
*A61B 3/032* (2006.01)
*G02B 27/01* (2006.01)

(52) U.S. Cl.
CPC ...... *G02B 27/017* (2013.01); *A61H 2201/1604* (2013.01); *A61H 2201/165* (2013.01); *A61H 2201/5007* (2013.01); *A61H 2201/5015* (2013.01); *A61H 2201/5097* (2013.01)

(56) References Cited

U.S. PATENT DOCUMENTS

| 2007/0064311 | A1* | 3/2007 | Park | G02B 27/0172 359/630 |
| 2007/0200927 | A1 | 8/2007 | Krenik | |
| 2010/0073469 | A1* | 3/2010 | Fateh | A61H 5/00 348/62 |
| 2010/0283969 | A1 | 11/2010 | Cooperstock et al. | |
| 2012/0071238 | A1* | 3/2012 | Bala | A63F 13/10 463/31 |
| 2012/0105473 | A1* | 5/2012 | Bar-Zeev | G02B 27/017 345/633 |
| 2012/0179076 | A1* | 7/2012 | Bavelier | A61H 5/005 601/37 |

FOREIGN PATENT DOCUMENTS

WO 2011067361 A1 6/2011
WO 2012000457 A1 1/2012

OTHER PUBLICATIONS

Extended European Search Report for Application No. 13837897.1 dated Apr. 28, 2016.

* cited by examiner

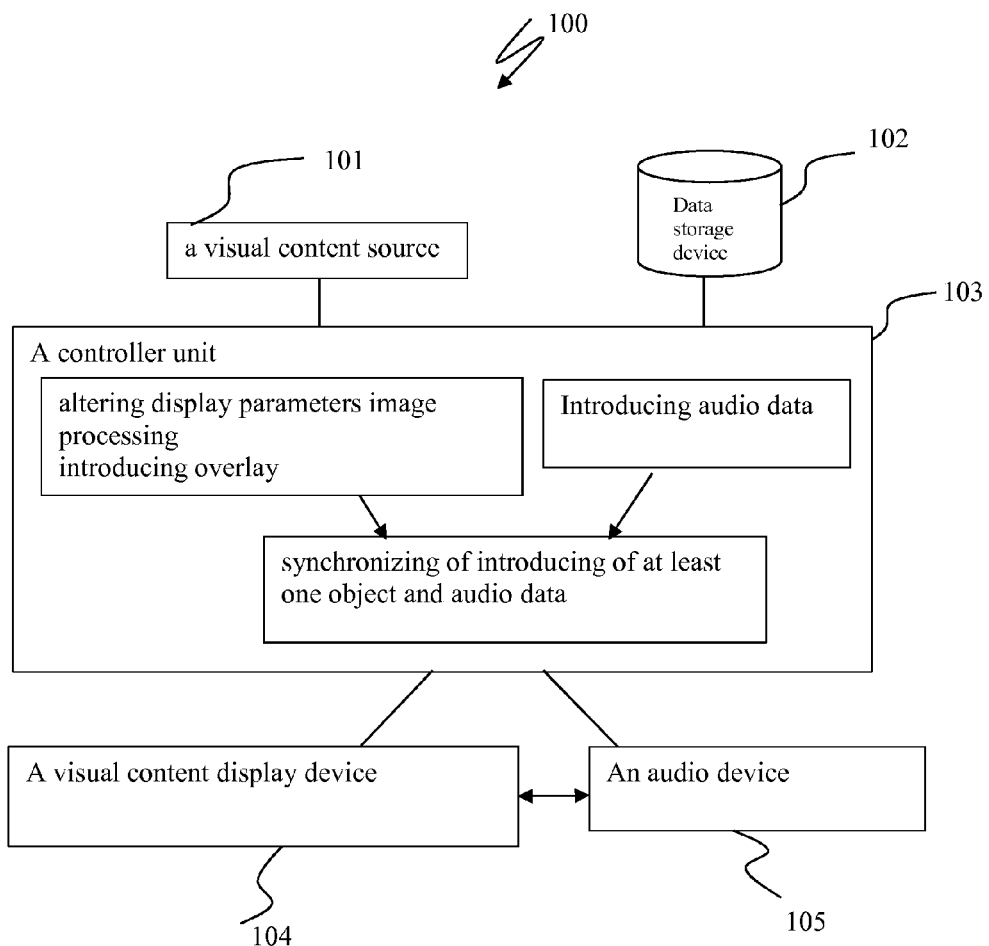
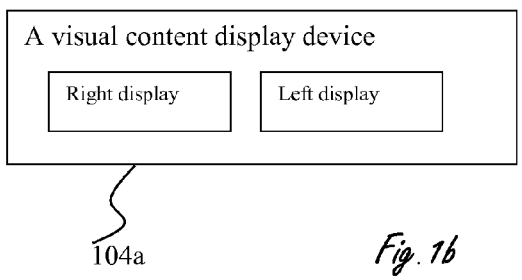 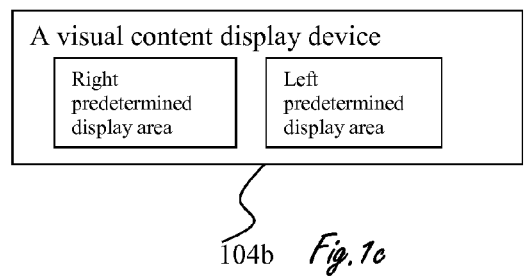
Fig. 1a
Fig. 1b   Fig. 1c

| Time units | | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| Left Eye | Brightness | -50% | 23% | 12% | 17% | 23% | 12% | 17% | 23% | 9% | 30% | 9% | 30% | 9% | 30% | 9% | 30% | 9% | 30% | 9% | 30% | 9% | 30% | 9% | 30% |
| Right eye | Brightness | 0% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% |
| Left Eye | Contrast | 5% | 27% | 38% | 32% | 27% | 38% | 32% | 27% | 50% | 18% | 50% | 18% | 50% | 18% | 50% | 18% | 50% | 18% | 50% | 18% | 50% | 18% | 50% | 18% |
| Right eye | Contrast | 0% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% |
| Left Eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Sharpness | 0% | -30% | -30% | -30% | -30% | -30% | -30% | -30% | -30% | -30% | -30% | -30% | -30% | -30% | -30% | -30% | -30% | -30% | -30% | -30% | -30% | -30% | -30% | -30% |

| Time units | | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|---|---|---|
| Left Eye | Brightness | 9% | 30% | 23% | 12% | 17% | 23% | -50% | 23% | 12% | 17% | 23% | 12% | 17% | 23% | 12% | 17% | 23% | 12% | 17% | 23% | -50% | 10% | 10% | 10% | 10% | 10% | 10% |
| Right eye | Brightness | -60% | -60% | -60% | -60% | -60% | -60% | 0% | -60% | -60% | -60% | -60% | -60% | -60% | -60% | -60% | -60% | -60% | -60% | -60% | -60% | -10% | 0% | 0% | 0% | 0% | 0% | 0% |
| Left Eye | Contrast | 50% | 18% | 27% | 38% | 32% | 27% | 5% | 27% | 32% | 27% | 27% | 38% | 32% | 27% | 38% | 32% | 27% | 38% | 32% | 27% | 5% | 12% | 12% | 12% | 12% | 12% | 12% |
| Right eye | Contrast | -60% | -60% | -60% | -60% | -60% | -60% | 0% | -60% | -60% | -60% | -60% | -60% | -60% | -60% | -60% | -60% | -60% | -60% | -60% | -60% | -10% | 0% | 0% | 0% | 0% | 0% | 0% |
| Left Eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Sharpness | -30% | -30% | -30% | -30% | -30% | -30% | -30% | -30% | -30% | -30% | -30% | -30% | -30% | -30% | -30% | -30% | -30% | -30% | -30% | -30% | 0% | 0% | 0% | 0% | 0% | 0% | 0% |

Fig. 5

| Time units | | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| Left Eye | Brightness | -50% | 23% | 12% | 17% | 23% | 12% | 17% | 23% | 9% | 30% | 9% | 30% | 9% | 30% | 9% | 30% | 9% | 30% | 9% | 30% | 9% | 30% | 9% | 30% |
| Right eye | Brightness | 0% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% |
| Left Eye | Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |

| Time units | | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|---|---|---|
| Left Eye | Brightness | 9% | 30% | 23% | 12% | 17% | 23% | -50% | 23% | 12% | 17% | 23% | 12% | 17% | 23% | 12% | 17% | 23% | 12% | 17% | 23% | -50% | 10% | 10% | 10% | 10% | 10% | 10% |
| Right eye | Brightness | -60% | -60% | -60% | -60% | -60% | -60% | 0% | -60% | -60% | -60% | -60% | -60% | -60% | -60% | -60% | -60% | -60% | -60% | -60% | -60% | -10% | 0% | 0% | 0% | 0% | 0% | 0% |
| Left Eye | Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye | Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |

Fig. 7

| Time units | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|
| Left Eye Brightness | -50% | 23% | 12% | 17% | 23% | 12% | 17% | 23% | 9% | 30% | 9% | 30% | 9% | 30% | 9% | 30% | 9% | 30% | 9% | 30% | 9% | 30% | 9% | 30% | 9% | 30% | 23% |
| Right eye Brightness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye Contrast | 5% | 27% | 38% | 32% | 27% | 38% | 32% | 27% | 50% | 18% | 50% | 18% | 50% | 18% | 50% | 18% | 50% | 18% | 50% | 18% | 50% | 18% | 50% | 18% | 50% | 18% | 27% |
| Right eye Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |

| Time units | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|
| Left Eye Brightness | 12% | 17% | 23% | -50% | 23% | 12% | 17% | 23% | 12% | 17% | 23% | 12% | 17% | 23% | 12% | 17% | 23% | -50% | 10% | 10% | 10% | 10% | 10% | 10% |
| Right eye Brightness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye Contrast | 38% | 32% | 27% | 5% | 27% | 38% | 32% | 27% | 38% | 32% | 27% | 38% | 32% | 27% | 38% | 32% | 27% | 5% | 12% | 12% | 12% | 12% | 12% | 12% |
| Right eye Contrast | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Left Eye Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Right eye Sharpness | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |

Fig. 9

| Time units | | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|---|
| Brightness | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Brightness | Right eye | 0% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | 0% |
| Contrast | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Contrast | Right eye | 0% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% | -60% |
| Sharpness | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Sharpness | Right eye | 0% | -30% | -30% | -30% | -30% | -30% | -30% | -30% | -30% | -30% | -30% | -30% | -30% | -30% | -30% | -30% | -30% | -30% | -30% | -30% | -30% | -30% | -30% | -30% | -30% | -30% | -30% |

| Time units | | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| Brightness | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Brightness | Right eye | -60% | -60% | -60% | 0% | -60% | -60% | -60% | -60% | -60% | -60% | -60% | -60% | -60% | -60% | -60% | -60% | -60% | -10% | 0% | 0% | 0% | 0% | 0% | 0% |
| Contrast | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Contrast | Right eye | -60% | -60% | -60% | 0% | -60% | -60% | -60% | -60% | -60% | -60% | -60% | -60% | -60% | -60% | -60% | -60% | -60% | -10% | 0% | 0% | 0% | 0% | 0% | 0% |
| Sharpness | Left Eye | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% | 0% |
| Sharpness | Right eye | -30% | -30% | -30% | 0% | -30% | -30% | -30% | -30% | -30% | -30% | -30% | -30% | -30% | -30% | -30% | -30% | -30% | 0% | 0% | 0% | 0% | 0% | 0% | 0% | fig. 11

SYSTEMS AND METHODS FOR TREATING AMBLYOPIA BY VISUAL STIMULATION OF THE BRAIN

CROSS-REFERENCE TO RELATED APPLICATIONS

The present application is a national phase entry under 35 U.S.C. §371 of International Application No. PCT/IL2013/050777, filed Sep. 15, 2013, which claims priority from U.S. Provisional Application No. 61/827,594, filed May 26, 2013, and U.S. Provisional Application No. 67/700,903, filed Sep. 14, 2012, all of which are incorporated herein by reference.

BACKGROUND OF THE PRESENT INVENTION

Amblyopia is characterized by poor or indistinct vision in an eye. It is one of the most common children ophthalmic disorders; it affects 1-5% of the population, and is generally associated with a history of strabismus, anisometropia, or deprivation of vision early in life by vision-obstructing disorders such as congenital cataract. Amblyopia is a developmental problem in the brain, not an organic problem in the eye. The part of the brain receiving the visual information from the affected eye is not stimulated properly, and develops abnormally. Blood oxygenation level-dependent (BOLD) functional magnetic resonance imaging (fMRI) is a widely used brain mapping technique, which can be used to evaluate the neural activity in the brain by measuring the blood flow to the local vasculature. More recently, fMRI has enabled the noninvasive investigation of brain cortical function in human amblyopia. It has been found that amblyopia is associated with lesions in the striate cortex (Brodmann area 17) and lateral geniculate nucleus (LGN) (*Int J Med Sci* 2012, 9 (1), 115-120).

An adult brain also poses some plasticity; however, it is much more limited than in an infant brain. However, there are certain conditions which can facilitate a circuit rewiring in a mature brain. At a cellular and molecular level, the adult plasticity is dynamically limited. Some of these "brakes" are structural, such as perineuronal nets or myelin, which inhibit neurite outgrowth. Others are functional, acting directly upon excitatory-inhibitory balance within local circuits (*J. of Neuroscience,* 2010, 30 (45), 14964-14971). It is contemplated that the plasticity in the childhood and adulthood may be induced by lifting these brakes through the exposure to a customized video content.

The conventional treatment of amblyopia involves full or part-time patching of the strong eye in order to force the use of the deficient eye. Owing to the risk to the strong eye, full-time patching is rarely employed nowadays. Since the critical period in humans is generally thought to end at 7-8 years of age, it is not surprising that the outcome of occlusion treatment is better in younger children than in those older than 6 years (*Invest Ophthalmol Vis Sci.* 2004, 45 (9), 3048-54). However, the full-time occlusion has been reported to be successful in children aged 9-14 years (*Eye (Lond).* 2004, 18 (6), 571-4), and the part-time occlusion (with patching of 2-6 hours per day) in children aged 7-17 years (*Arch Ophthalmol.* 2005, 123 (4), 437-47); in most children aged 7-12 years, the improvement in acuity persists for at least a year after termination of patching (*Arch Ophthalmol.* 2007, 125 (5), 655-9). Even patients aged 13-17 years may still respond positively to the part-time patching if they have not been treated previously, although it is not yet known whether their visual acuity improvement is permanent (*Arch Ophthalmol.* 2005, 123 (4), 437-47). However, the greatest threat to a successful patching treatment of amblyopia in little children is a lack of compliance.

Thus it is strong felt and unmet need to provide an amblyopia treatment through a visual stimulation system and method.

SUMMARY OF THE PRESENT INVENTION

It is an object of the present invention to provide a system useful for treating amblyopia by visual stimulation of the brain. The system comprises: i) a headmountable visual content display device, comprising at least one display comprising at least one predefined displaying area; ii) a controller unit; iii) a visual content source. The controller unit is configured to modify over time presentation of a video content displayed on at least one predefined displaying area by means selected from the group consisting of image processing or changing at least one display parameter affecting image presentation of at least one displaying area according to a predetermined regime.

The system as described, wherein the display device is configured to substantially isolate user's eyes from external visual disturbances.

The system as described above, wherein the display device is operatively connected to an audio device configured to provide audio stimulation according to the predetermined regime.

The system as described above, wherein the controller unit additionally comprises a data storage device adapted to be operatively connected to the controller unit configured to store the predetermined regime.

The system as described above, wherein the controller unit comprises a graphic processing unit configured to alter at least one image parameter according to the predetermined regime.

The system as described above, wherein at least one display parameter is selected from the group containing brightness, contrast, saturation, sharpness, resolution, or other conventional parameters and combinations thereof.

The system as described above, wherein the controller unit is additionally configured to insert at least one overlay of at least one object on at least one displaying area.

The system as described above, wherein the controller unit is additionally configured to introduce at least one flicker event on at least one displaying area.

The system as described above, wherein the controller unit is additionally configured to trigger audio data configured to be coherently connected to inserting of at least one generated overlay of at least one object according to the predetermined regime.

The system as described above, wherein the controller unit is additionally configured to synchronize the audio data and inserting of at least one generated overlay of at least one object according to the predetermined regime.

The system as described above, wherein the visual content source selected from the group consisting of a video game console, cable modem, a television, a computer, a digital camera, a camcorder, a DVD, a mobile phone, a portable media player, an offline video content storage device, and a network online streaming video content.

It is further purpose of the present invention to provide a protocol useful for treating amblyopia by visual stimulation of the brain. The protocol comprises steps of: i) obtaining a system useful for treating amblyopia; ii) streaming a video content and a sound track to a controller unit; iii) modifying presentation of the video content displayed on at least one displaying area; iv) displaying the modified video content to at least one eye; v) providing an audio stimulation. The modifying step is selected from the group consisting of image processing or changing at least one display parameter affecting image presentation.

The protocol as described above, wherein the modifying step is configured to be implemented according to the predetermined regime.

The protocol as described above, wherein the image processed video content is configured to be displayed in a dichoptic presentation selected from the group consisting of Side by Side, Frame Sequential, and Field Sequential presentation.

Yet another aim of the present invention is to provide a predetermined regime useful for increasing the cerebral blood flow in the brain of an amblyopic patient. The regime comprises at least one step of modifying the presentation of a video content displayed on at least one displaying area by means selected from the group consisting of image processing or changing at least one display parameter affecting image presentation at the frequency configured to be in the range of 0.5-60 Hz. The modification is configured to increase the cerebral blood flow in the brain in comparison to a regime lacking the aforementioned modifications.

The regime as described above, wherein the regime additionally comprises introducing at least one flicker event.

The regime as described above, wherein the regime additionally comprises triggering an audio stimulation configured to be administered to at least one ear.

The regime as described above, wherein the regime is additionally configured to insert at least one overlay of at least one object on the video content displayed on said at least one displaying area.

The regime as described above, wherein the modifying step is configured to alter the level of at least one display parameter within the range of 99% to +99% of the intensity of at least one display parameter of the streamed video content.

The regime as described above, wherein the step of inserting at least one overlay of at least one object is configured to be coherently connected to triggering of the audio stimulation.

The regime as described above, wherein the regime is configured to operate in real time.

A visual stimulation regime for a binocular image display device is further provided. This regime comprises at least one visibly noticeable intensity alteration of at least one image parameter defining a video image as presented on at least one display area. The intensity alteration of the image parameter is configured to be the range of −99% to +99% of the intensity of the defined video's image parameter, wherein the image parameter is selected from the group consisting of contrast, brightness, sharpness, saturation, resolution or other conventional parameters and any combination thereof.

The visual stimulation regime as defined above additionally comprises at least one visibly noticeable intensity alteration of at least one value of at least one image parameter defining a video image as presented on at least one display areas. The intensity alteration of the image parameter values is configured to be in the range of −99% to +99% of the intensity of the defined video's image parameter, wherein the image parameter is selected from the group consisting of contrast, brightness, sharpness, saturation, resolution or other conventional parameters and any combination thereof.

A visual stimulation regime for an image display device is additionally provided. The regime comprises at least one visibly noticeable intensity alteration of at least one image parameter defining a video image as presented on at least one display area. The intensity alteration of the image parameter is configured to be in the range of −99% to +99% of the intensity of the defined video's image parameter, wherein the image parameter is selected from the group consisting of contrast, brightness, sharpness, saturation, resolution or other conventional parameters and any combination thereof.

The regime as defined above additionally comprises at least one visibly noticeable intensity alteration of at least one value of at least one image parameter defining a video image as presented on at least one display areas. The intensity alteration of the image parameter values is configured to be the range of −99% to +99% of the defined video's image parameter, wherein the image parameter is selected from the group consisting of contrast, brightness, sharpness, saturation, resolution or other conventional parameters and any combination thereof.

Any regime as described above, wherein alteration of the volume level administered to at least one ear is in conjunction to an intensity alteration of at least one value of at least one image parameter defining a video image as presented on at least one display areas.

BRIEF DESCRIPTION OF FIGURES OF THE PRESENT INVENTION

FIG. 1 schematically illustrates the system for the visual stimulation of the brain.

FIG. 2 schematically illustrates two types of dichoptic presentation: Side by Side and Frame Sequential.

FIG. 5 to FIG. 12 illustrate four different embodiments of a predetermined protocol.

DETAILED DESCRIPTION OF THE PRESENT INVENTION

Figure 2:
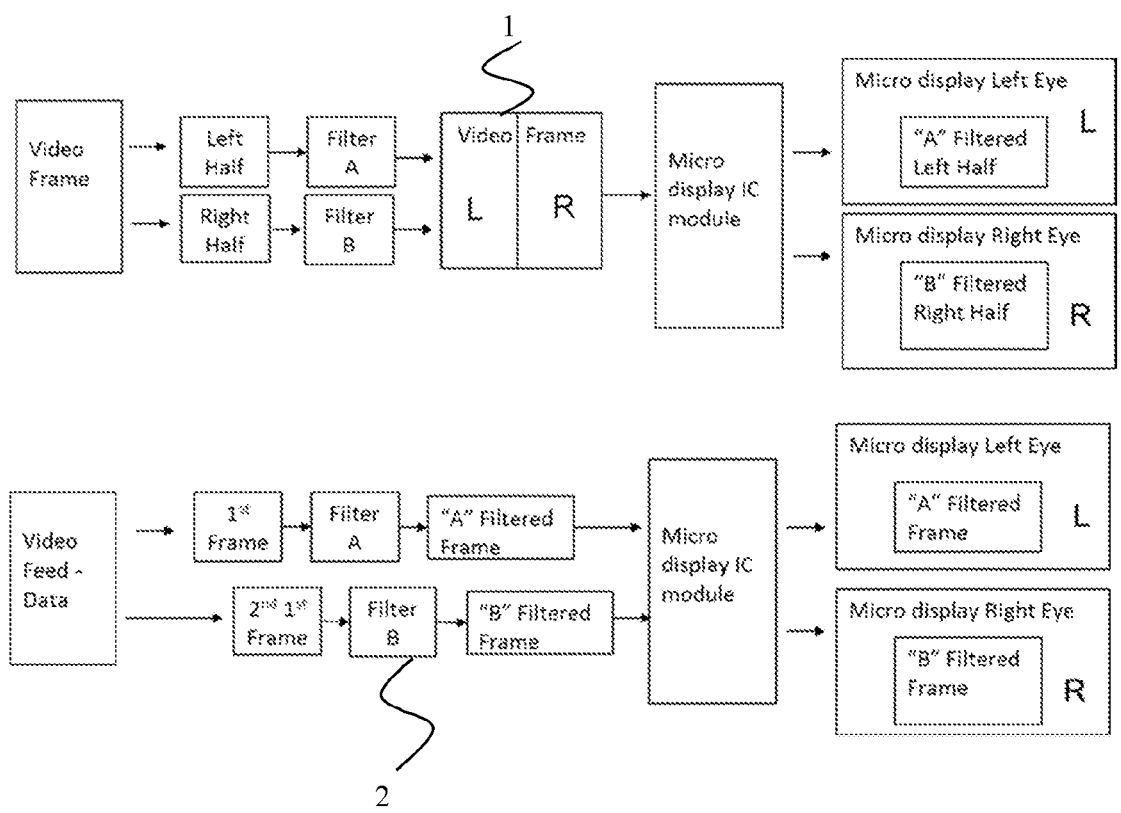

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide product and method of the invention described herein.

In the following description the terms weak/deficient/amblyopic and dominant/strong eye are used interchangeably. Furthermore, the terms the cerebral blood flow in the brain and perfusion of the brain are also used interchangeably.

The present invention relates to a system for treating amblyopia through the visual stimulation of the brain.

The System

The reference is made to FIG. 1a that in exemplified way illustrates the system (100) in one of the embodiments of the present invention. The system comprises a visual content source (101), a data storage device (102), a controller unit (103), a headmountable visual content display device (104) and an audio device (105).

The headmountable display device (104) is configured to isolate the user's eyes from external visual disturbances such as ambient light. In one of the embodiments the display device can fit tightly to the user's face, as goggles; in other embodiments the display device may have shades that prevent the light reaching the eyes of a user. The visual content display device can be represented by several embodiments. In one of the embodiments of the present invention (FIG. 1b) the headmountable binocular display device (104a) comprises left and right displays, each comprising one displaying area, configured to display the video content to the two eyes. In other embodiments of the present invention the headmountable visual content display device (104b) comprises a single display, by way of a non-limiting example, Such a display is of the type used in cellular phones, with left and right predefined displaying areas configured to display the video content to the two eyes. The visual content display device may also be coupled to an audio device (105) which can be represented by a set of headphones or speakers. The headphones or speakers are configured to comprise various transducers technologies known in the art such as of electrostatic, orthodynamic, dynamic, electret, balanced armature, the Heil air motion transformer (AMT), piezoelectric film, ribbon planar magnetic, magnetostriction, plasma-ionisation and electromagnetic technologies.

The controller unit (103) is connected to the video content display device and configured to alter in some embodiments the display parameters affecting image presentation on the binocular display device according to the predetermined regime. In other embodiments of the present invention the controller unit is configured to modify the display parameters affecting image presentation of at least one predefined displaying area according to the predetermined regime. In some other embodiments of the present invention the controller may comprise a graphic processing unit (GPU) configured to alter the display parameters affecting image presentation according to the predetermined regime. The display parameters affecting image presentation defined as brightness, contrast, saturation, resolution, sharpness, or any other parameter known in the art and any combination thereof.

In other embodiments of the present invention the controller unit (103) is configured to alter the video content presentation displayed on the display device by image processing according to the predetermined regime. Moreover, the image processed video content is configured to be displayed in a dichoptic presentation such as is known in the art for presenting 3D videos, FIG. 2, discloses, by way of non-limiting example, the group consisting of Side by Side (1), Frame Sequential (2), and Field Sequential presentation.

Moreover, the controller unit (103) can generate or trigger at least one overlay of at least one object and at least one flicker event according to the predetermined protocol. The controller unit is configured to trigger audio data coherently connected with inserting of at least one object and configured to synchronize the appearance of at least one object and the triggered audio data.

The controller unit can be connected to the visual content source via TRS minijack, RCA jack, TOSLINK, BNC, D-subminiature, RCA jack, Mini-DIN, 3 RCA jacks, VIVO, DVI, SCART, HDMI, Display Port connector, FireWire, WiFi and Bluetooth.

The data storage device (102) is connected to the controller unit and configured to store the predetermined protocol, at least one file with at least one overlaying object and audio data. In some embodiments of the present invention the data storage device can be connected to the controller unit via PATA, IDE, EIDE, SATA, SCSI, SAS, Fiber Channel, IEEE 1394, USB, WiFi, and Bluetooth connectors. In the preferred embodiments of the present invention the data storage device is connected to the controller unit via wireless technology such as WiFi or Bluetooth.

In some embodiments of the present invention the visual content source (101) can be represented in a non-limiting way by a visual content source selected from the group consisting of a video game console, a television, a computer, a digital camera, a camcorder, a DVD, a mobile phone, a portable media player, an offline video content storage device, and a network online streaming video content or any other content source known in the art.

The Protocol

Figure 3:
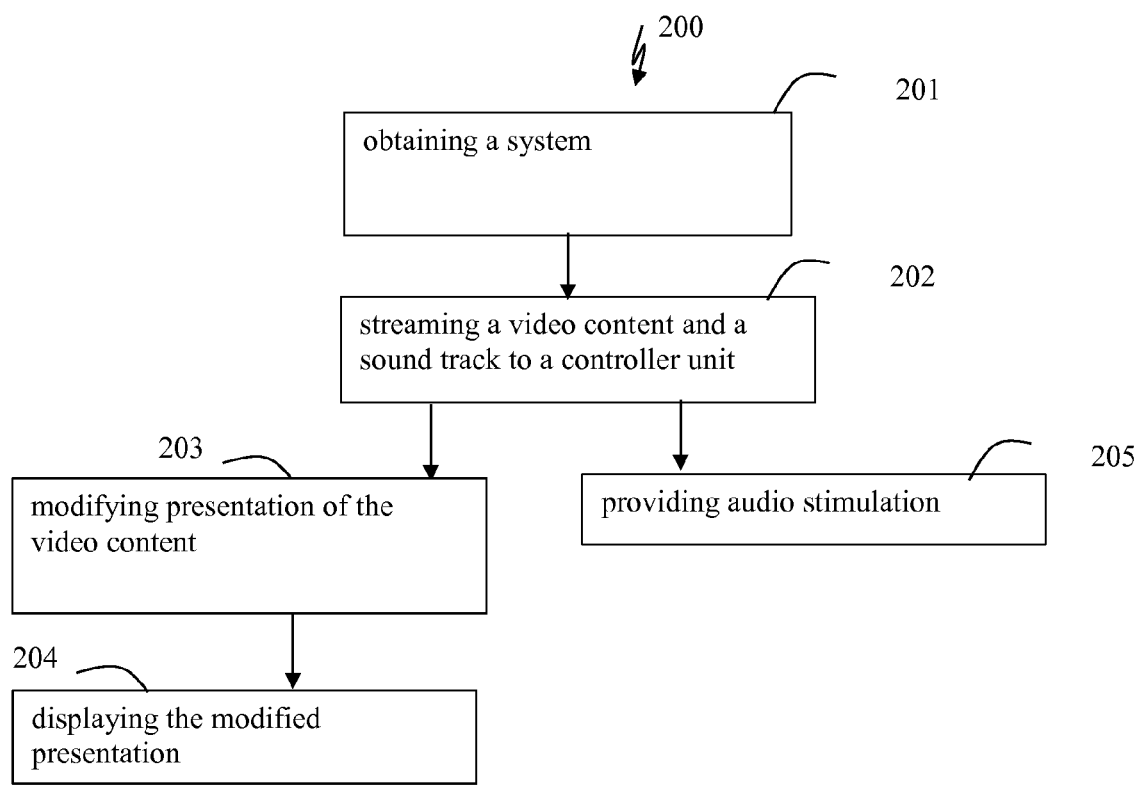
FIG. 3 illustrates a flow chart of the protocol for the visual stimulation of the brain.

The reference is made to FIG. 3 that schematically illustrates a protocol (200) useful for treating amblyopia by visual stimulation of the brain comprising the following steps:
  i. obtaining a system useful for treating amblyopia (201);
  ii. streaming a video content and a sound track to a controller unit (202);
  iii. modifying presentation of said video content displayed on at least one displaying area (203);
  iv. displaying said modified presentation to at least one eye (204);
  v. providing an audio stimulation (205).

In some embodiments of the present invention the modifying step is achieved by image processing of the video content according to the predetermined regime. In other embodiments the modifying step comprises altering the display parameters affecting image presentation of at least one displaying area. The audio stimulation is provided to at least one ear.

The Regime

Figure 4:
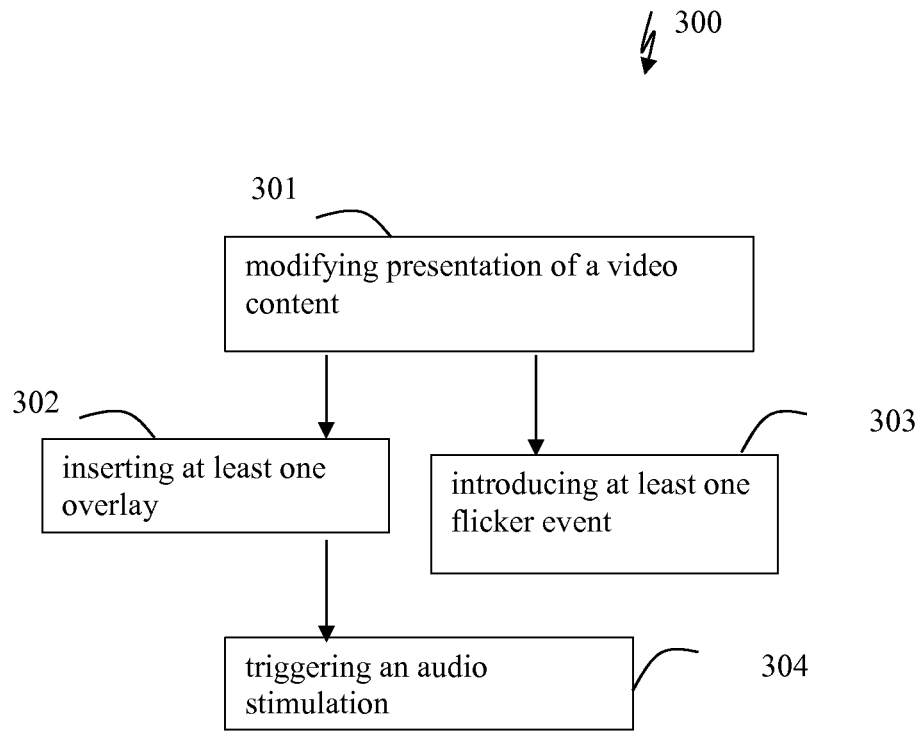
FIG. 4 illustrates a flow chart of the dynamic predetermined protocol.

The reference is made to FIG. 4 that schematically illustrates a dynamic predetermined regime (300) useful for treating amblyopia by visual stimulation of the brain comprises:
  i. modifying over at least one time unit presentation of a video content displayed on at least one displaying area by means selected from the group consisting of image processing or changing at least one display parameter (301);
  ii. inserting at least one overlay of at least one object on the video content displayed on at least one displaying area (302);
  iii. introducing at least one flicker event (303);
  iv. triggering an audio stimulation configured to be administered to at least one ear configured to be coherently connected to the appearance of at least one overlay (304);

The regime is configured to modify the display parameters affecting image presentation over at least one time unit in some embodiments of the right and left displays, and in other embodiments of the left and right predefined displaying areas. In one of the embodiments of the present invention the regime is configured to alter the presentation of the video content by implementation of the image processing techniques known in the art. In some embodiments of the present invention at least one time unit is configured to have a duration of less than a second. In other embodiments of the present invention at least one time unit is configured to have a duration of at least one second.

The display parameters affecting image presentation to be modified are brightness, contrast, saturation, sharpness, resolution, or any other parameter known in the art and combinations thereof. Furthermore, the regime is configured to modify the intensity of the display parameters affecting image presentation within the range of −99% to +99% of the intensity of the same parameters of the original streamed video content.

The regime is configured to modify the presented video content in such way that, for example, an enhanced sharp and\or bright video streaming is displayed to the deficient eye during most of the protocol, whereas the dominant eye will be exposed to a dampened i.e. dim image with poor video image quality. Additionally the enhanced video and dampened video streaming is accompanied by an audio stimulation. The audio stimulation can be exemplified in a non-limiting way by the elevated volume administered to the ear which is next to the deficient eye and by the reduced volume administered to the second ear.

Furthermore, the regime may also be configured to insert at least one overlay of at least one object stored as a file at the data storage device over the streamed video content, such that this modified video is displayed to the deficient eye. Additionally the regime is also configured to trigger an audio signal stored as a file at the data storage device that accompanies the appearance of the aforementioned object. This audio stimulation is configured to be administered to the ear positioned at the side of the deficient eye, or alternately the opposite ear. For example in non-limiting way, the controller unit insets the overlay of a bouncing ball and simultaneously the controller unit trigger the audio signal "ball" or elevates the volume of the audio streaming. Moreover, the regime is also configured to introduce at least one flicker event displayed to the deficient eye accompanied by an audio signal such as in non-limiting way by the sound of thunder or another attention focusing sound. The flicker occurs when the brightness is abruptly and momentarily dropped to a minimal value for time intervals sufficiently long to be noticed by a human eye, alternatively, the flicker occurs by displaying a sequence of frames which are not part of the original sequence of frames of the presented video content. The predetermined regime is configured to operate in real time.

Furthermore, a visual stimulation regime for a binocular image display device comprises at least one visibly noticed intensity alteration of at least one image parameter defining a video image presented on at least one display area (by way of clarification, the term "visibly noticed intensity alteration" shall mean alteration of any visual stimulus allied to the brain via the eyes); where the intensity alteration of the image parameter is configured to be in the range of −99% to +99% of the defined video's image parameter, wherein the image parameter is selected from the group consisting of contrast, brightness, sharpness, saturation, resolution etc. and any combination thereof. Additionally this regime comprises at least one visibly noticed intensity alteration of at least one value of at least one image parameter defining a video image presented on at least one display area; where the intensity alteration of the image parameter values is configured to be in the range of −99% to +99% of the defined video's image parameter, wherein the image parameter is selected from the group consisting of contrast, brightness, sharpness, saturation, resolution and any combination thereof.

Moreover, a visual stimulation regime for an image display device comprises at least one visibly noticed intensity alteration of at least one image parameter defining a video image presented on at least one display area; where the intensity alteration of the image parameter is configured to be in the range of −99% to +99% of the defined video's image parameter, wherein the image parameter is selected from the group consisting of contrast, brightness, sharpness, saturation, resolution etc. and any combination thereof. This particular regime additionally comprises at least one visibly noticed intensity alteration of at least one value of at least one image parameter defining a video image presented on at least one display areas; where the intensity alteration of the image parameter values is configured to be the range of −99% to +99% of the defined video's image parameter, wherein the image parameter is selected from the group consisting of contrast, brightness, sharpness, saturation, resolution or any other parameter known in the art and any combination thereof.

It is well accepted that during increased neural activity, the cerebral metabolism rate of glucose (CMRglu) is increased and concurrently, cerebral blood flow (CBF) and cerebral blood volume (CBV) are elevated. For example the relative cerebral metabolic rate of oxygen $CMRO_2$ in the visual cortex increased significantly during visual stimulation consisted of a circular black and white checkerboard, reversing at 8 Hz and its magnitude change was 0.3-0.7 times the CBF change. A weak positive correlation between CBF in visual cortex and $CMRO_2$ changes was observed, suggesting that the $CMRO_2$ increase is proportional to the CBF change (*Magnetic Resonance in Medicine* 1999 41, 1152-1161).

In other research an elevation of retinal blood flow by the luminance flicker stimulation in humans it has been discovered (*Investigative Ophthalmology & Visual Science* 2011, 52 (1) 274-277). Furthermore, it was found that changes in the cerebral blood flow in the primary visual cortex were 16%±16% and 68%±20% for the photic flicker stimulation at 2 Hz and 8 Hz, respectively. Whereas the changes in the cerebral blood volume were 10%±13% and 21%±5% for 2-Hz and 8-Hz stimulation, respectively (*J Cereb Blood Flow Metab*, 2001 21, (5), 608-612). The experiments on cats demonstrated that the optic nerve head (ONH) blood flow and [$K^+$] increased during the flicker stimulus (*Investigative Ophthalmology & Visual Science* 1995 36, (11), 2216-2227). The largest increase in $K^+$ potential occurred at 30 Hz whereas the largest ONH blood flow increase occurred at 40 Hz.

The regime of the present invention is configured to increase the cerebral blood flow in the brain.

Non-Limiting Examples of the Predetermined Regime

The tables in FIG. 5 to FIG. 12 illustrate the examples of the predetermined regime where the left eye is a deficient eye and a strong eye is the right eye. The term time unit presented in the tables can embody fractions of a second or at least one second.

Figure 6:
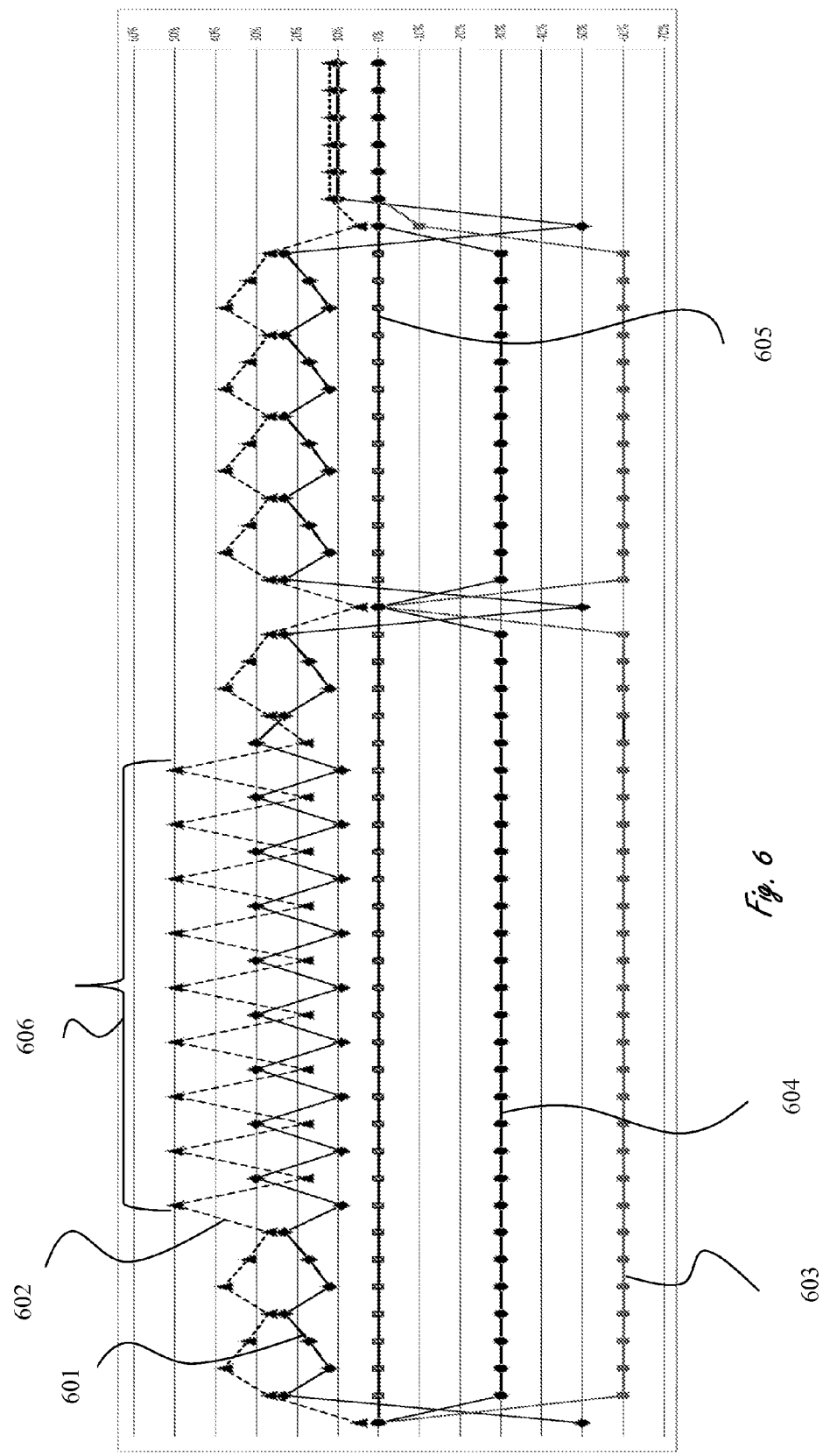

The FIG. 5 and FIG. 6 illustrate the regime where the brightness, contrast (603) and sharpness (604) of the dichoptic presentation are lowered for the right eye during the entire regime except at the starting point. The brightness (601) and contrast (602) of the video streaming displayed to the deficient eye is enhanced during the regime, while the sharpness (605) is left unchanged. Furthermore, the duration of the time unit of the contrast and brightness alteration presented to the left eye within the range of time units 8-25 is 1/16 of a second (606). Thus the left eye receives visual stimulation at the frequency of 8 Hz. The duration between time units 45 to 50 represent a resting time where the stimulation is minimal or non-existent, to allow the brain a recovery period and is preferably but not necessarily part of the regime.

Figure 8:
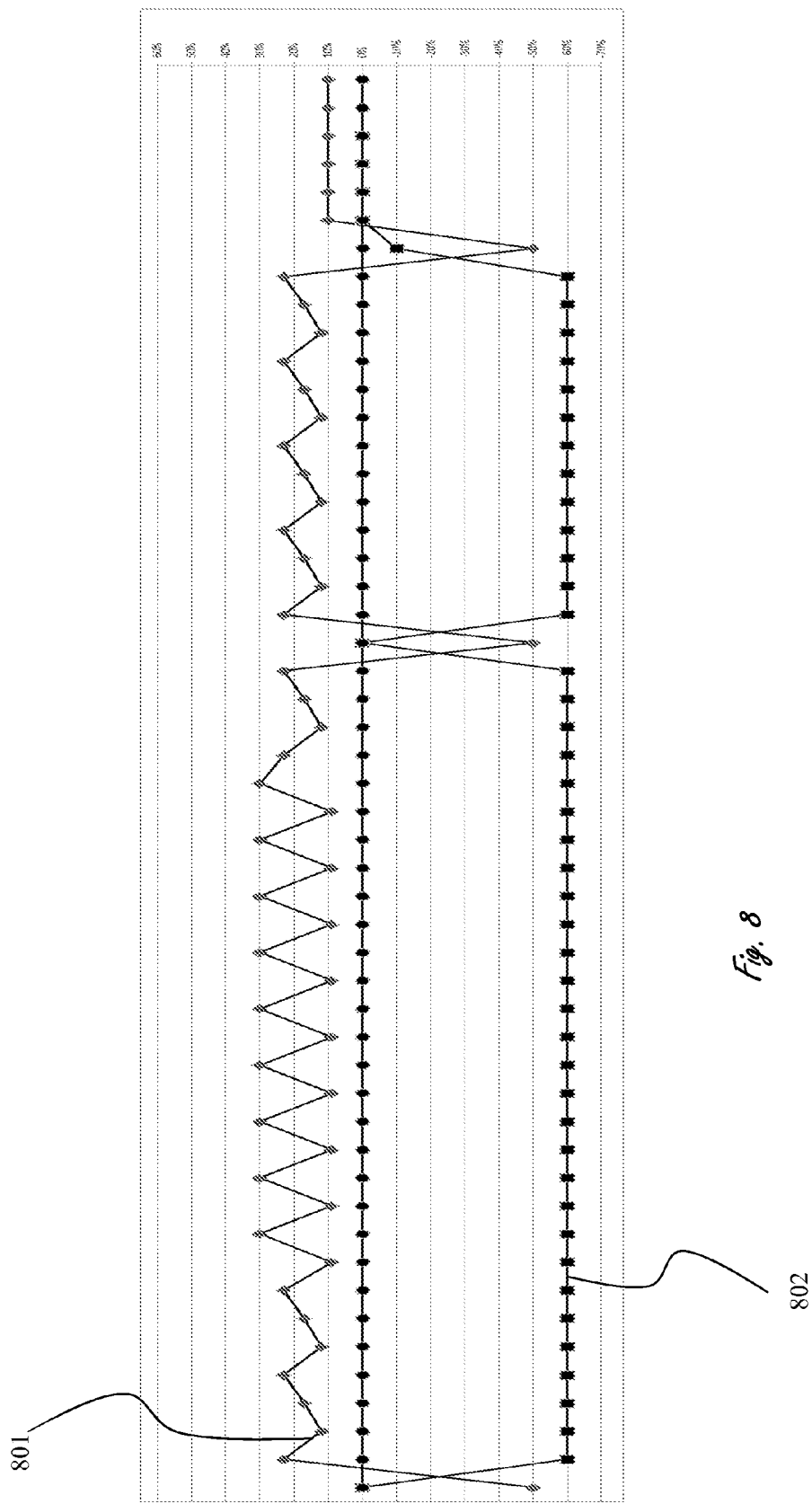

FIG. 7 and FIG. 8 illustrate the regime where only the brightness of the dichoptic presentation is changed for the left (801) and right (802) eyes. The brightness of the video streaming displayed to the deficient eye is enhanced during most of the regime, while the brightness of the video streaming displayed to the strong eye is lowered during the entire regime except at the starting point.

Figure 10:
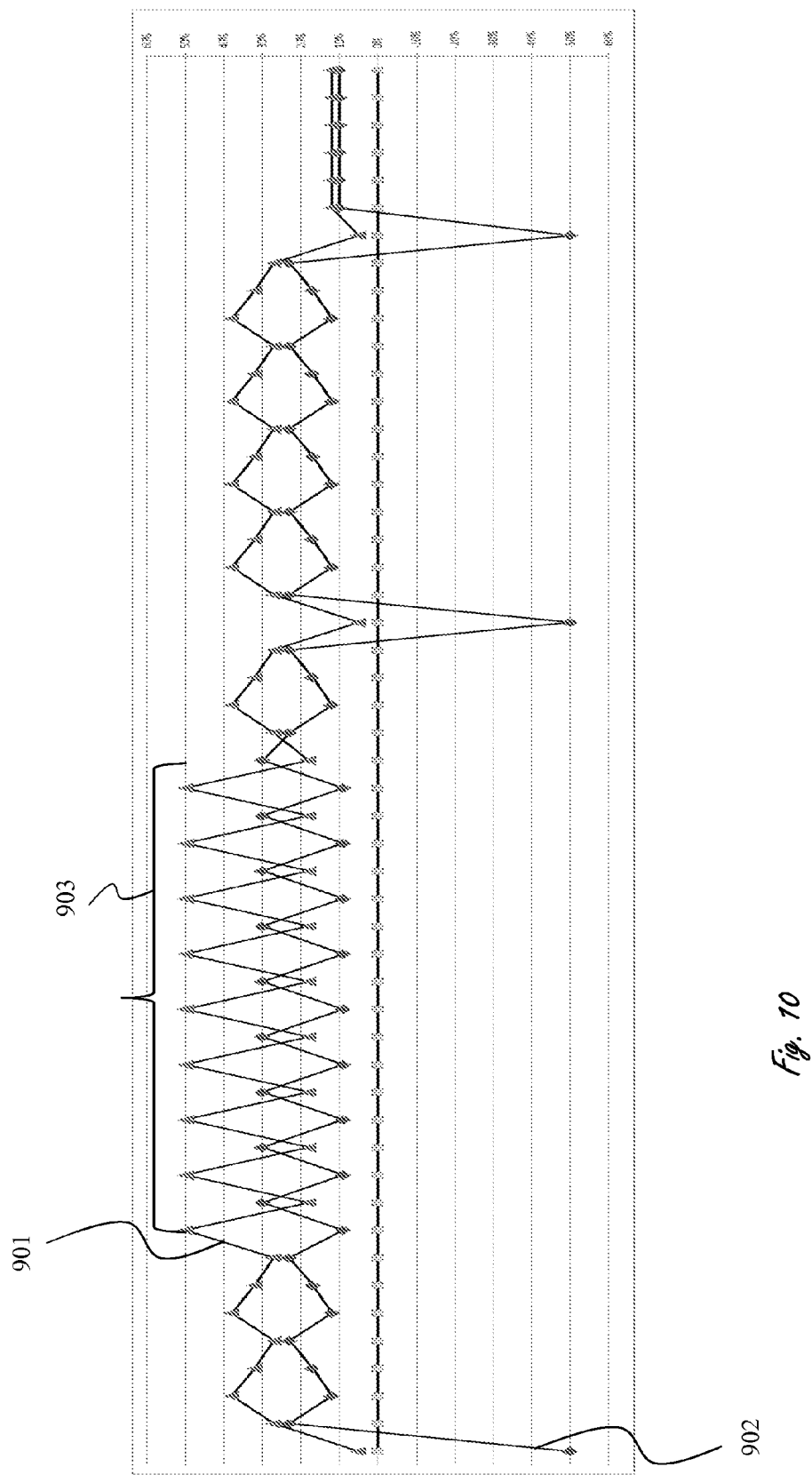

FIG. 9 and FIG. 10 illustrate the regime where the brightness (902) and contrast (901) of the dichoptic presentation are enhanced only for the left eye. Furthermore, the duration of the time unit of the contrast and brightness alteration presented to the left eye within the range of time units 8-25 is 1/16 of a second (903). Thus the left eye receives visual stimulation at the frequency of 8 Hz.

Figure 12:
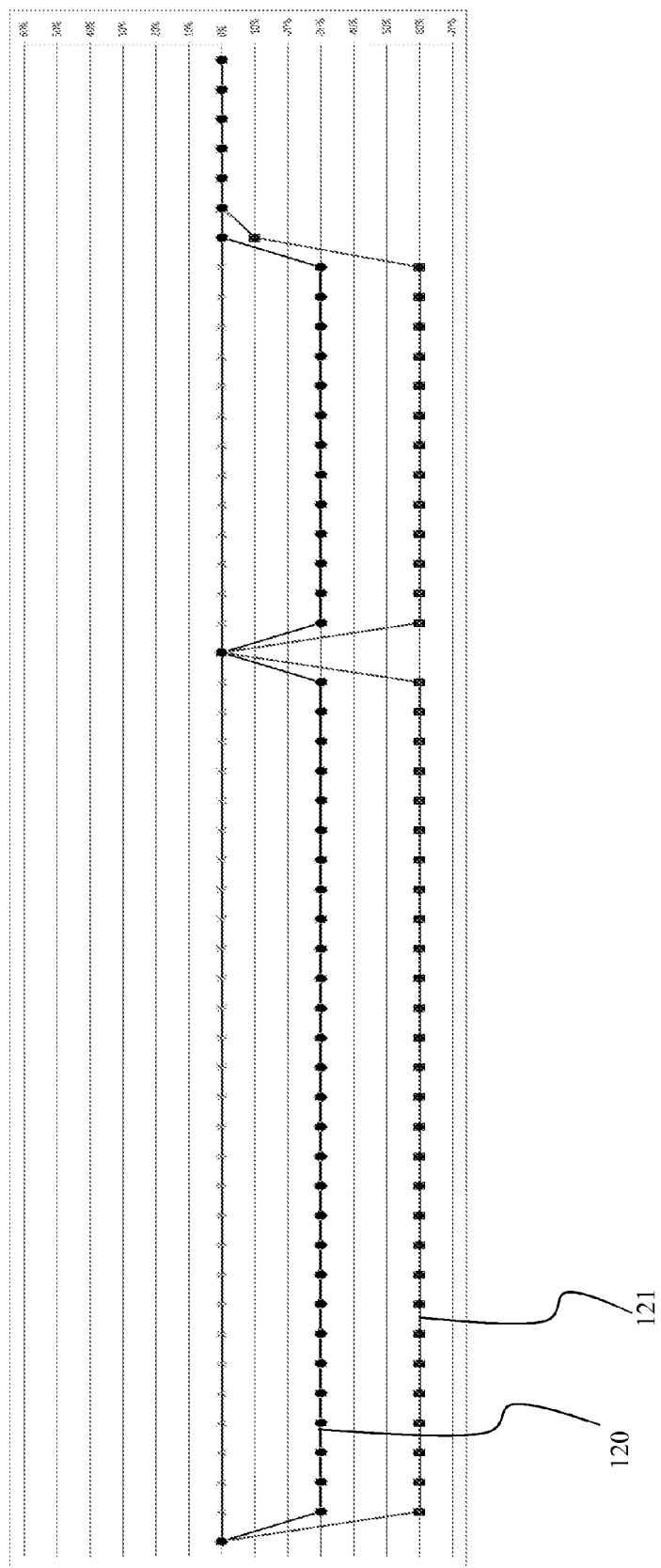

FIG. 11 and FIG. 12 illustrate the regime where the brightness, contrast (121) and sharpness (120) of the dichoptic presentation are dampened only for the right eye.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system useful for treating amblyopia by stimulation configured to increase brain blood flow of a user, comprising:
   a head mountable visual display device having at least one displaying area and coupled to a controller unit, the controller unit configured to alter presentation of a video image in a streaming video content in real time for presenting the video image to each eye of the user in accordance with a pre-determined stimulation regime;
   an audio device configured to provide an audio stimulation to each ear of the user according to the pre-determined stimulation regime;
   the pre-determined stimulation regime further including at least one visibly noticed intensity alteration of an image parameter defining the video image presented on at least one display area of the head mountable visual display device;
   the controller unit further configured to provide the pre-determined stimulation regime;
   wherein, the pre-determined stimulation regime applies a modifying step by altering the image parameter at a frequency configured to be in a range of 0.5-60 Hz; and
   wherein the image parameter is selected from the group consisting of contrast, brightness, sharpness, saturation, resolution, and any combination thereof; and
   wherein the audio device further provides the audio stimulation according to the pre-determined stimulation regime by differing ear volume administered proximal to a side of the user having a deficient eye from that administered proximal to another side of the user not having the deficient eye.

2. The system of claim 1, wherein the intensity alteration of the image parameter is configured to be in a range of −99% to +99% of the image parameter defining the presented video image.

3. The system of claim 1, wherein the audio device is configured to provide audio stimulation according to said predetermined stimulation regime by elevating ear volume administered proximal to the side of the user having the deficient eye, and by reducing ear volume administered proximal to another side of the user not having the deficient eye.

4. The system of claim 1, wherein said controller unit additionally comprises a data storage device adapted to be operatively connected to said controller unit configured to store said predetermined stimulation regime.

5. The system of claim 1, wherein said controller unit comprises a graphic processing unit configured to alter said at least one display parameter according to said predetermined stimulation regime.

6. The system of claim 1, wherein said at least one display parameter is displayed enhanced to the deficient eye and displayed dampened to the fellow eye.

7. The system of claim 1, wherein said controller unit is additionally configured to insert, based on the pre-determine stimulation regime, at least one overlay object of at least one object on said at least one displaying area.

8. The system of claim 7, wherein said controller unit is additionally configured to trigger audio stimuli associated with at least one overlay object according to said predetermined stimulation regime.

9. The system of claim 7, wherein said controller unit is additionally configured to synchronize audio to the insertion of at least one overlay of at least one object according to said predetermined stimulation regime.

10. The system of claim 1, wherein said controller unit is additionally configured to introduce based on the pre-determined stimulation regime at least one flicker event on said at least one displaying area.

11. The system of claim 10, wherein said controller unit is additionally configured to insert the at least one flicker event displayed to the deficient eye, wherein the flicker event occurs by displaying a sequence of frames that are not part of original frames in the video.

12. A process useful for treating amblyopia by stimulation configured to increase brain blood flow of a user comprising:
   placing a head mountable visual display device on a user, the device having at least one displaying area and coupled to a controller unit, the controller unit configured to alter presentation of a video image in a streaming video content in real time for presenting the video image to each eye of the user in accordance with a pre-determined stimulation regime;
   having an audio device operatively connected to the head mountable visual display, the audio device configured to provide an audio stimulation to each ear of the user according to the pre-determined stimulation regime;
   having the pre-determined stimulation regime further including at least one visibly noticed intensity alteration of an image parameter defining the video image presented on at least one display area of the head mountable visual display device;
   having the controller unit further configured to provide the pre-determined stimulation regime;
   wherein, the pre-determined stimulation regime applies a modifying step by altering the image parameter at a frequency configured to be in a range of 0.5-60 Hz; and
   wherein the image parameter is selected from the group consisting of contrast, brightness, sharpness, saturation, resolution, and any combination thereof; and
   wherein the pre-determined stimulation regime is affecting properties of the audio stimulation in conjunction to the modifying step of the image parameter; and
   wherein the audio device further provides the audio stimulation according to the pre-determined stimulation regime by differing ear volume administered proximal to a side of the user having a deficient eye from that administered proximal to another side of the user not having the deficient eye.

13. The process of claim 12, wherein said visual display device is configured to display in a dichoptic presentation selected from the group consisting of Side by Side, Frame Sequential, and Field Sequential presentation.

14. A predetermined regime useful for increasing the cerebral blood flow in the visual system of an amblyopic patient comprising
modifying at least one displaying area by changing a display parameter affecting display presentation at the frequency configured to be in the range of 0.5-60 Hz;
altering at least one visibly noticed intensity of the display parameter defining a video image presented on at least one display area of a head mountable visual display device;
selecting the display parameter from the group consisting of contrast, brightness, sharpness, saturation, resolution, and any combination thereof; and
wherein the pre-determined visual stimulation regimen is affecting properties of audio stimulation in conjunction to the modifying step of the display parameter; and
wherein an audio device further providing the audio stimulation according to the pre-determined stimulation regime by differing ear volume administered proximal to a side of the user having a deficient eye from that administered proximal to another side of the user not having the deficient eye; and
wherein said modification is configured to increase the cerebral blood flow in the visual system in comparison to a regime lacking said modifications.

15. The regime of claim 14, wherein said predetermined stimulation regime additionally comprises introducing at least one flicker event.

16. The regime of claim 14, wherein said predetermined stimulation regime additionally comprises triggering an audio stimulation configured to be administered to at least one ear by elevating ear volume administered proximal to the side of the user having the deficient eye, and by reducing ear volume administered proximal to another side of the user not having the deficient eye.

17. The regime of claim 14, wherein said predetermined stimulation regime is additionally configured to insert at least one overlay of at least one object on a video content displayed on said at least one displaying area.

18. The regime of claim 14, wherein said modifying step is configured to alter the level of said at least one display parameter within a range of 99% to +99% of an intensity of said at least one display parameter of a streamed video content.

19. The regime of claim 14,
wherein said predetermined stimulation regime additionally comprises triggering an audio stimulation configured to be administered to at least one ear; and
wherein said predetermined stimulation regime is additionally configured to insert at least one overlay of at least one object on said video content displayed on said at least one displayed area; and
wherein said step of inserting said at least one overlay of said at least one object is configured to be coherently connected to said triggering of said audio stimulation.

20. The regime of claim 14, wherein said predetermined stimulation regime is configured to operate in real time.

21. A visual stimulation regime for a binocular image display device comprising
providing at least one visibly noticeable intensity alteration of at least one display parameter to at least one display area; said intensity alteration of said display parameter is applied to said at least one display area in a range of −99% to +99% of said intensity of said display parameter;
providing an audio device configured to provide an audio stimulation to each ear of a user according to the pre-determined stimulation regime;
the pre-determined stimulation regime further including at least one visibly noticed intensity alteration an image parameter defining the video image presented on at least one display area of the head mountable visual display device;
the controller unit further configured to provide the pre-determined stimulation regime;
wherein, the pre-determined stimulation regime applies a modifying step by altering the image parameter at a frequency configured to be in a range of 0.5-60 Hz; and
wherein the image parameter is selected from the group consisting of contrast, brightness, sharpness, saturation, resolution, and any combination thereof; and
wherein the audio device further provides the audio stimulation according to the pre-determined stimulation regime by differing ear volume administered proximal to a side of the user having a deficient eye from that administered proximal to another side of the user not having the deficient eye.

22. The regime of claim 21, wherein said predetermined stimulation regime additionally comprises at least one visibly noticeable intensity alteration of at least one value of at least one image parameter defining a video image as presented on the at least one display area; said intensity alteration of said image parameter values is configured to be in the range of −99% to +99% of said intensity of said image parameter defining the presented video image.

23. A visual stimulation regime for an image display device comprises
providing at least one visibly noticeable intensity alteration of at an image parameter defining a video image as presented on at least one display area; said intensity alteration of said image parameter is configured to be in a range of −99% to +99% of said intensity of said image parameter, wherein said image parameter is selected from the group consisting of contrast, brightness, sharpness, saturation, resolution or other conventional parameters and any combination thereof;
providing an audio device configured to provide an audio stimulation to each ear of a user according to the pre-determined stimulation regime;
the pre-determined stimulation regime further including at least one visibly noticed intensity alteration said image parameter defining the video image presented on at least one display area of the head mountable visual display device;
the controller unit further configured to provide the pre-determined stimulation regime;
wherein, the pre-determined stimulation regime applies a modifying step by altering said image parameter at a frequency configured to be in a range of 0.5-60 Hz; and
wherein said image parameter is selected from the group consisting of contrast, brightness, sharpness, saturation, resolution, and any combination thereof; and
wherein the audio device further provides the audio stimulation according to the pre-determined stimulation regime by differing ear volume administered proximal to a side of the user having a deficient eye from that administered proximal to another side of the user not having the deficient eye.

* * * * *